United States Patent [19]
Rothenberg

[11] Patent Number: 4,862,503
[45] Date of Patent: Aug. 29, 1989

[54] VOICE PARAMETER EXTRACTOR USING ORAL AIRFLOW

[75] Inventor: Martin Rothenberg, Dewitt, N.Y.

[73] Assignee: Syracuse University, Syracuse, N.Y.

[21] Appl. No.: 145,295

[22] Filed: Jan. 19, 1988

[51] Int. Cl.⁴ .............................................. G10L 7/10
[52] U.S. Cl. ........................................................ 381/48
[58] Field of Search ...................... 381/41–46, 381/48–49, 36–40; 369/513.5

[56] References Cited

U.S. PATENT DOCUMENTS

| | | | |
|---|---|---|---|
| 2,672,512 | 3/1954 | Mathes | 179/1.5 |
| 2,803,801 | 8/1957 | Cunningham | 324/77 |
| 3,245,403 | 4/1966 | Lieberman | 128/2 |
| 3,327,057 | 6/1967 | Coker | 179/1 |
| 3,327,058 | 6/1967 | Coker | 179/1 |
| 3,335,225 | 8/1967 | Campanella et al. | 179/1 |
| 3,345,979 | 10/1967 | Miura et al. | 128/2 |
| 3,368,039 | 2/1968 | Clapper | 179/1 |
| 3,881,059 | 4/1975 | Stewart | 381/41 |
| 3,906,936 | 9/1975 | Habal | 381/46 |
| 4,063,035 | 12/1977 | Appelman et al. | 179/1 SP |
| 4,273,959 | 6/1981 | Tuda et al. | 381/48 |
| 4,718,096 | 1/1988 | Meisel | 381/43 |

OTHER PUBLICATIONS

M. Rothenberg, *A New Inverse-Filtering Technique for Deriving the Glottal Air Flow Waveform During Voicing*, 53 J. Acou. Soc. Am, 1632, (1973).

M. Rothenberg, *Measurement of Airflow in Speech*, 20, J. Speech and Hearing Res. 155, (1977).

Primary Examiner—Gary V. Harkcom
Assistant Examiner—John A. Merecki
Attorney, Agent, or Firm—Wall and Roehrig

[57] ABSTRACT

A technique for extracting voice parameters from oral or combined oral and nasal air flow involves having a test subject or patient pronounce a vowel sound that has a high first formant into a pneumotachographic device which produces an output voiced speech waveform that includes the mean air flow. This output signal is appropriately filtered to remove the formant frequencies and produce a smoothed glottal waveform approximation. From the pneumotachograph output waveform and smoothed glottal waveform are derived a peak value P, a minimum value L, glottal wave period $T_O$ and average value M for the glottal waveform. The amplitude and wave center value can readily be calculated, and from these the open quotient $Q_O$ can be derived which represents the ratio of the duration of the open portion B of the glottal wave cycle to the entire period $T_O$ thereof. These values can be recorded directly, or can be used to synthesize a replica of the subject's glottal airflow for either one typical vocal fold vibratory cycle or a number of successive cycles. The technique can be carried out using digital techniques.

19 Claims, 2 Drawing Sheets

VOICE PARAMETER EXTRACTOR USING ORAL AIRFLOW

BACKGROUND OF THE INVENTION

This invention relates to the quantitative measurement of the parameters of human speech, especially to those relating to the functioning of the human larynx. The invention is more specifically directed to method and apparatus for processing oral or combined oral and nasal airflow waveflows to provide information concerning laryngeal flow. In voiced speech, vowel sounds are formed by a glottal source waveform on which are superimposed vocal tract resonances or formants. The glottis is the passageway between the vocal folds when they are open. The glottal waveform, which represents the volume velocity of the flow of air through the larynx as the vocal folds open and close in a quasi-periodic manner, normally has in each cycle an "open" portion which represents the outrush of air when the glottis is open, and a relatively flat, "closed" portion which represents the relative cessation of airflow when the vocal folds are closed along all or most of their length. The formants are resonances produced by the vocal tract—that is, the throat, mouth, sinuses, and nasal passages—that selectively amplify certain of the harmonics of the glottal waveform to produce the acoustic qualities associated with the various vowels and consonants of the language.

In very efficient voices, the glottal airflow waveform during a normal voiced speech sound will exhibit a slow rise when the glottis is opening, and then a sharp drop when the glottis closes, with a flat section between the open portions where there is little or no airflow occurring. In most persons, the waveform is much rounder than the ideal, and the glottal waveform more approximates a truncated sine wave shape which would result in a weaker voice for a given expenditure of airflow.

It is also true that in most persons the closed portion of the glottal wave is not absolutely flat, and where there is some problem preventing the vocal folds from closing completely, there may be a significant amount of airflow even during the closed portion. This can sometimes be heard as a breathiness or huskiness of voice. An otherwise unexplained increase in airflow during the closed portion over the level normal for a given speaker could also mean that there is a polyp or other growth in the larynx on or near the vocal folds. Though the details of the glottal air flow pattern can vary greatly between individuals, for the purpose of monitoring the efficiency of the vibration pattern of the vocal folds in modulating the air stream to produce acoustic energy, the parameters of the waveform that are now recognized to have the most significance are (1) the period of the vibratory cycle, which determines the vocal pitch, (2) the average air flow during that period, which determines the rate of deflation of the lungs, (3) the offset of the minimum value of the waveform from zero flow, which indicates the degree to which the vocal fold closure is incomplete, (4) the peak to peak amplitude of the waveform during the cycle, which reflects the mobility of vocal folds as they vibrate, and (5) the percentage of each glottal cycle during which there is a significantly increased air flow, which reflects directly the period during which the vocal folds are separated during their oscillatory cycle and indirectly the degree to which the vocal folds are pressed together (adducted) or held apart (abducted).

Ideally, a health practitioner should be able to chart these voice parameters of a patient from week to week to show the progress of disease or of therapy.

The need for such standardized quantitative measures of the functioning of the larynx is one that has long been in search of a solution. At present, there are only two non-invasive methods available for clinical use to estimate or describe the vibratory pattern of the vocal folds, namely electroglottography and inverse-filtering of the airflow or pressure waveform at the mouth.

Electroglottography basically measures the variation and degree of contact between vocal folds during that part of the glottal cycle in which the folds are in contact with each other. Changes in electrical resistance at the throat are measured by a device that contacts the patient's skin and indicates the change in resistance as the vocal folds meet and come into tighter contact. Unfortunately, this technique gives no absolute measure of the degree of contact of the vocal folds and no real information about the portion of the glottal cycle in which the vocal folds are out of contact, beyond the duration of that period.

In an inverse filtering technique either the pressure waveform outside the mouth, as recorded from a suitable microphone, or the waveform of the volume of air flow exiting the mouth or the mouth and nose combined, as recorded by a suitable pneumotachograph, are electronically filtered to produce the waveform of the volume air flow through the glottis. For clinical purposes, inverse-filtering the airflow rather than the pressure is preferred because only the airflow measurement results in a known zero level and permits ready calibration of airflow scale of the resulting glottal flow waveform.

In the air flow inverse-filtering technique, a wire-screen peripheral flow pneumotachograph mask, such as the Rothenberg mask, produces an oral volume velocity waveform adequate for inverse-filtering. An electronic circuit or equivalent computer algorithm permits inverse-filtering of the mask output. By "inverse-filtering", what is meant is that the major formants are removed from the oral waveform by an electronic filter having a frequency response that is the inverse of that of the vocal tract. Because the formant frequencies and bandwidths can change from one patient to another, depending not only on the internal geometry of the patient's vocal tract, but on the precise vowel being spoken, the adjustments of a manual formant inverse-filtering system must be carefully selected by a trained technician. Consequently, voice parameter analysis using this technique has been a rather arduous affair, conducted by only a few highly trained specialists.

Although this technique has been used by many voice research laboratories and some research-oriented facilities, the need to adjust the inverse-filter parameters for each subject, that is, to adjust the frequency and damping of the lowest two or three vocal tract resonances, has made this system impractical for general clinical use.

To overcome this problem, there have been many proposals to develop a computer-based automated inverse-filtering algorithm. Although these may eventually be of value, as presently proposed such automated inverse-filtering schemes can produce gross errors if the program is in error. Unfortunately, such errors are most likely to occur for abnormal voices, and such voices are quite often those of the patients who could benefit most from voice analysis. Such voices typically are breathy or have a significant nasality. Both of these conditions are contrary to the assumptions on which the automated inverse-filtering schemes would be predicated. Sophisticated schemes for automated inverse-filtering which are sufficiently robust to handle an adequately wide variety of voice conditions are not forthcoming.

Thus, to be of value for the clinical evaluation of vocal function, an ideal automatic voice parameter extracting technique should be able, for a wide range of normal and abnormal voice types, to produce a reliable numerical estimate of the duration of each glottal vibratory period measured as well as the value during that period of maximum or peak value, the mean value, and the minimum value of the glottal volume velocity during that period, and an open quotient value which would represent the ratio of the duration of the portion of the glottal cycle during which the air flow is significantly increased from its minimum value to the duration of the entire glottal vibratory period. However, prior to this invention, there have been no suitable techniques developed for automatically extracting these parameters.

OBJECTS AND SUMMARY OF THE INVENTION

Accordingly, it is an object of this invention to provide method and device for producing a quantitative record of the efficiency of the human voice source and particularly of the quality of the glottal airflow waveform.

It is a more specific object to provide automatic extraction, from oral or combined oral and nasal airflow, of the parameters of the glottal airflow waveform that relate to the clinically significant features of the vocal fold vibratory pattern, and to produce those parameters in a form that is suitable for use by otolaryngologists, speech therapists, and other practitioners such as voice and singing coaches.

It is another object of this invention to produce a record of the condition of an individual's vocal airflow parameters so that the progress of the condition of the individual's laryngeal voice source can be charted and understood.

It is another object of this invention to provide a voice parameter extraction technique which is reliable and highly repeatable, and which is also rapid and simple to use.

In accordance with an aspect of this invention, a technique for extracting the voice parameters can be used with oral or oral and nasal airflow that is produced during voiced speech. In this technique, the patient pronounces a vowel sound into a pneumotachograph which produces an output signal that represents the waveform of the volume velocity of the airflow during the vowel, and includes the mean d.c. airflow. The patient is asked to pronounce a vowel having a high first formant such as "ah" or "ae" in the vowels in the words "pop" and "pap", respectively. Though any speech context can be used, a word such as "bop" or "pop" (or "bap" or "pap") is preferably chosen because an unvoiced bilabial stop ("p") adjoining the desired vowel sound allows the air pressure in the lungs to be readily measured in the mouth during the period of oral closure. This procedure is explained in Rothenberg, *A New Inverse-Filtering Technique for Deriving the Glottal Airflow Waveform During Voicing*, Journal of the Acoustical Society of America, Vol. 53, 1973, pages 1632-1654.

A low-pass filtering operation is performed on the amplified and prefiltered pneumotachograph output signal to produce a smooth version of the glottal airflow waveform in which the formants of the pronounced vowel are almost entirely suppressed. Then, from this waveform and the filtered output are derived the peak value P, the minimum value L, and the period $T_0$ of the glottal wave, as well as the average or mean airflow value M for a given period $T_0$. The amplitude A of the glottal waveform is derived as the difference between the peak and minimum values, and the center value $\overline{M}$ of the glottal wave is derived as the difference between the mean airflow value M and the minimum value L. The open quotient $Q_0$, which represents the ratio of the duration of the open portion B of the glottal wave cycle (in which the patient's vocal folds are not in contact) to the duration of the entire cycle $T_0$, is derived from these measured parameters using an approximation of the glottal wave. A suitable approximation for this purpose can be a truncated sine wave, in which the open quotient $Q_0$ can be derived from the following relationship:

$$\frac{\sin(\pi Q_0) - \pi Q_0 \cos(\pi Q_0)}{1 - \cos(\pi Q_0)} = \frac{\pi \overline{M}}{A}$$

The values of P, L, and $Q_0$ can be provided on a display and/or printed out to produce a record of the voice parameters of the patient. Equipment for carrying out this technique can include a pneumotachograph instrument into which the patient pronounces the vowel, a low-pass filter system for prefiltering that has an input coupled to the pneumotachograph instrument and which filters the output signal of the instrument to produce a waveform in which the formants of the pronounced vowels above the second are suppressed. Further signal processing circuitry has inputs coupled to the prefilter system to receive the waveform and to derive from this waveform an estimate of the extent of a single period of the glottal waveform, with a duration $T_0$, as well as an estimate of the peak value P, the minimum value L and the mean value M of the glottal waveform during the period selected. A calculating device is input with the values P, L, $T_0$, and M to produce estimates of the values of the amplitude A and the wave center value $\overline{M}$ of the glottal waveform, and further, e.g., by means of a programmed lookup table or equivalent approximating equation, to find the open quotient $Q_0$ corresponding to the input values of A and $\overline{M}$. The low-pass prefilter system can include a linear-phase (that is, constant delay) low-pass filter having an input coupled to receive the output signal of the pneumotachograph instrument. The input of a band-pass filter is coupled to the output of the low-pass prefilter which has a pass band that extends approximately from the lowest frequency $F_0$ to the highest $F_0$ expected from the glottal waveform of the pronounced vowel. This produces a filtered AC output. A zero-crossing detector measures the glottal period $T_0$ from the output of the band pass filter. An approximate inverse-filter circuit consisting of an antiresonance or simple notch filter is coupled to the output of the low-pass prefilter for reducing the energy in the waveform near formant frequency $F_1$ of the pronounced vowel. The output of this notch filter is coupled to the input of a second low-pass filter, with a roll-off frequency slightly below the lowest expected first formant frequency but well above the expected range of voice fundamental $F_0$ ($f_{-3\ dB}$ at approximately $\frac{1}{2}$ $F_1$). This low-pass filter, which should have little or no overshoot removes almost all remaining formant energy and furnishes a smoothed version of the glottal waveform to another circuit designed to measure the minimum value, which is also furnished with the output of the zero-crossing detector, to derive the minimum value L of the glottal airflow waveform during each selected glottal period. A third low-pass filter, which can be coupled to the output of the second low-pass filter and has a roll-off frequency below the frequency $F_0$ of the glottal waveform, produces the value of the mean airflow M when sampled at the end of each selected glottal period. The output of the prefilter is also coupled to the input of a peak detector circuit, as is the output of the zero-crossing detector which defines each glottal period. The output of the peak detector system during each selected glottal period is interpreted as the peak value P of the glottal waveform. Adders combine the peak value P and the minimum value L to produce the amplitude value A, and combine the mean airflow value M and the minimum value L to produce the wave center value $\overline{M}$.

In an alternative arrangement, a digitizer is input with the waveform from the output of the pneumotachographic instrument and produces a sequence of numerical sample values, with the low-pass filtering, bandpass and inverse-filtering being carried out by selectively combining the numerical sample values to produce a derivative sequence of values that represent the respective filtered waveforms. The peak value P, minimum value L, and mean airflow value M and the values of $\overline{M}$ and $Q_0$ computed from P, L and M can be derived directly from the digitized waveforms by a programmed microprocessor device that is input with the derivative sequences of numerical values.

The technique of this invention bypasses the pitfalls inherent in the more conventional inverse-filtering, and provides a cost effective and robust means for obtaining those parameters relasing to glottal airflow that have the greatest significance for clinical applications. The parameter values can be displayed or printed directly or can instead be used to reconstruct a stylized representation of the patient's glottal waveform.

In this technique, the average lung pressure during the vowel can be estimated form the oral pressure during a neighboring unvoiced stop by means of a pressure sensor mounted on the pneumotachographic mask and coupled through the corner of the mouth into the oral cavity. Although this is not essential to the method, im-lung pressure is often helpful in interpreting the significance of the glottal flow waveform.

In its basic form, this technique uses, for each estimated glottal period, the peak value P of the slightly smoothed oral flow waveform, the minimum value L of an oral flow waveform that is low-pass filtered at approximately $\frac{1}{2}$ $F_1$, where $F_1$ is the estimated or typical frequency of the first formant for the vowel spoken, and the average or mean value M of the oral flow waveform. This technique differs form previous methods in that precise formant measurements are not required; rough aural monitoring of the vowel to verify that it is an open vowel with a high first formant is sufficient to assure reliable operation.Nasality is permitted, provided that the sum of oral and nasal flow is used instead of oral flow alone where significant nasality is present. This technique is more robust than previous techniques, because there are no subjectively determined parameters that can cause gross errors if set incorrectly during the measurement procedure. The stylized waveform that can be reconstructed from the measured parameters permits easy intrasubject and intersubject comparisons.

To simplify the process of voice parameter extraction, this technique utilizes a number of special features of the voice waveform and of vocal tract acoustics during an open vowel (such as "ah" or "ae"). In such vowels, during the most open phase of the glottal cycle, there is little acoustic energy at the vocal tract resonances in the oral flow waveform. Thus, the positive peak of the oral wave does not differ much from the positive peak of the glottal wave, and can be used as an estimate for it. This occurs because there is little formant energy added by the glottal source near the positive peak of the flow waveform, since the motion of the vocal folds during that part of the vibratory cycle is relatively smooth and uninterrupted. Also, the strong oscillations that can be generated at the lower formants during the preceding closed phase are quickly damped when the glottis opens and absorbs some of the energy. This damping process is aided by the added dissipation of the formant energy (increase in formant bandwidth) caused by the flow resistance of the pneumotachograph mask. Sound absorbing materials can also be added at the mouth to improve accuracy by further increasing the formant damping, if the resultant change in voice quality is acceptable.

As long as $F_0$ is less than about $\frac{1}{3}$ of $F_1$, the minimum value of the glottal waveform is well represented by the minimum value of the low-pass filtered output of the approximate inverse-filter. There are two cases to consider. If vocal folds are oscillating in an abducted state, the glottal airflow and oral airflow are both relatively sinusoidal at the fundamental frequency $F_0$, so that a low-pass filter with a cutoff significantly above $F_0$ will retain the gross features of the entire waveform and therefore have both maximum and minimum values that approximate those of the glottal waveform. If, on the other hand, the vocal folds are less abducted, the glottal flow waveform will tend to have a relatively flat portion near the minimum value, as parts of the vocal folds come into contact and the glottal area consequently changes less during the period of contact. During this flatter portion, the output of the low-pass filter will have time to approach the value of the minimum level of glottal flow. Thus, the minimum value of the waveform taken from the output of an appropriate low-pass filter with cutoff set at about $\frac{1}{2}$ $F_1$ will be very close to the actual minimum of the glottal waveform. To improve accuracy of this approximation, an anti-resonance can be added that is set at approximately the frequency and damping of the first formant $F_1$. This will allow the low-pass filter to be set somewhat higher in frequency and yet adequately reject the first formant acoustic oscillations, thus extending the range of the voice fundamental frequencies over which this technique is usable.

For the purpose of visualizing the underlying vocal fold motions from the measured parameter values, the glottal waveform can be represented by a smoothly varying waveform, such as a sinusoid, that is truncated at its negative side, and offset from the level of zero flow by a value representing the air "leakage" during the interval of vocal fold contact. This waveform would be constructed so as to conform to the glottal parameters measured by the system. An additional feature representing the asymmetry of the glottal flow pulse can be added, but since this asymmetry is caused mostly by vocal tract acoustics, and not vocal fold motion, it is of less clinical interest. Therefore this can be omitted in most cases. This underlying model for the glottal flow pulse permits computation of the clinically important feature, termed the glottal duty cycle or open quotient $Q_0$ from the negative and positive extermes and the average value.

The glottal pulse asymmetry can be estimated from the phase relationship between the fundamental component $F_0$ and the lower harmonics, at $2F_0$, $3F_0$, etc., which for a symmetrical pulse would be in such a phase relationship as to all reach their maximum value simultaneously at one instant in every cycle. Alternatively, the pulse asymmetry can be computed from a moment calculation, as the thrid central moment is zero for any symmetrical waveform. This estimate can be used, as desired, to correct the computation of open quotient $Q_0$, and may be included in the reconstructed representation of the glottal pulse.

An estimate of the extent of each fold vibratory period to be analysed is required for determining the maximum and minimum of the glottal waveform, and for computing the mean value M. This estimate can be obtained by filtering the oral waveform through a linear-phase (i.e., constant delay) band-pass filter whose pass band lies between the lowest expected fundamental frequency $F_{0L}$ and a point between the lowest expected first formant frequency $F_1$ and the highest expected fundamental frequency $F_{OH}$. The glottal period can be assumed to be the interval between negative-going zero crossings of the resulting waveform, corrected for the delay introduced by the filter. However, any other similarly robust measure of the glottal period may be used, provided that it employs a cycle-by-cycle determination. The signal from an electroglottograph (EGG) may be useful for this purpose, if a strong EGG signal is available.

The system employing the principles described hereinabove can find the value of the open quotient $Q_0$ from the values of the wave center value $\overline{M}$, and the amplitude A (which is the peak P minus the minimum L), by using a waveform model relating the open quotient $Q_0$ to the values of $\overline{M}$ and A. Under the assumption of a truncated symmetrical sinusoid, this function takes the form of the following relationship which implicity determines $Q_0$:

$$\frac{\sin(\pi Q_0) - \pi Q_0 \cos(\pi Q_0)}{1 - \cos(\pi Q_0)} = \frac{\pi M}{A}$$

The technique of this invention can be implemented using standard linear or analog type filters and circuits, or, more preferably, can be implemented by digital filtering and other algorithms on a microcomputer that has analog/digital capabilities added by means of a data acquisition board. To increase formant damping, the pneumotachograph mask could have an airflow resistance about twice the value that is normally used, that is, about one cm $H_2O$-second per liter.

The results of the analysis of a patient's voice can be presented both as a tabulation of the numerical glottal waveform parameters for each glottal cycle analysed, and as a reconstructed waveform having, for each cycle, the shape of a sinusoid clipped at the bottom at at an amplitude that results in the measured open quotient $Q_0$, and having a peak-to-peak amplitude and offset from zero flow corresponding to the measured values of A and L respectively. Glottal pulse asymmetry can be inserted, if desired, but as it does not relate significantly to the functioning of the vocal folds, asymmetry may not be necessary for most clinical applications. Aperiodicity in the glottal flow waveform may be represented by measuring and portraying a sequence of successive glottal cycles. Moreover, a second channel can be used to record the intraoral pressure of the neighboring bilabial stops, as sampled, for example, through a tube at the corner of the mouth, to permit the estimation tracheal pressure. The data can be recorded directly in a computer in digital form or on a multi-channel FM instrumentation-type tape recorder and then played back into the computer for analysis.

The above and other objects, features and advantages of this invention will be more fully understood from the ensuing description of a preferred embodiment, which should be considered in connection with the accompanying drawing.

DETAILED DESCRIPTION OF PREFERRED EMBODIMENTS

Figures 1, 2, 2A:
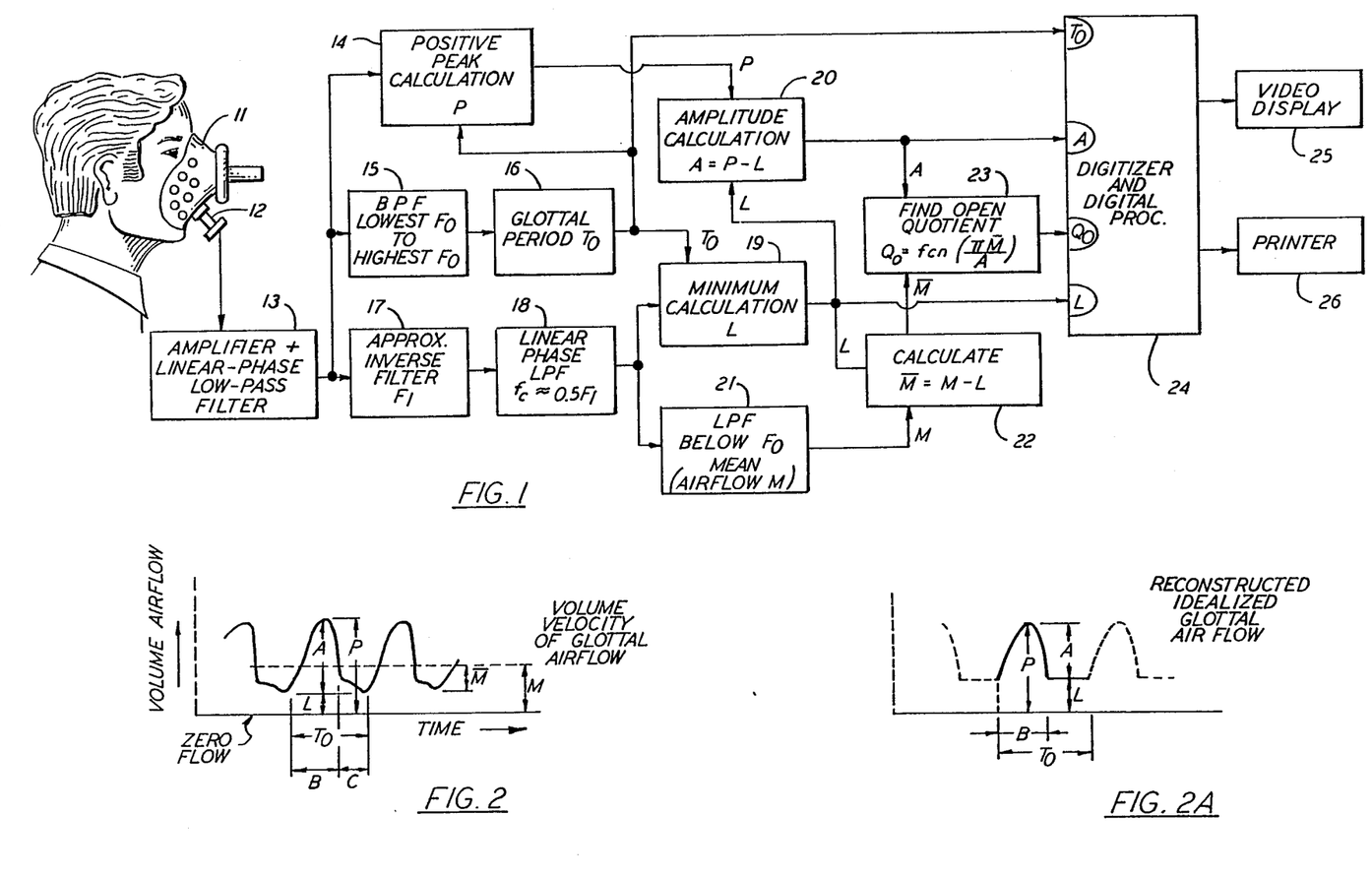
FIG. 1 is a schematic circuit drawing of a first embodiment of this invention.
FIG. 2 is a chart for explaining the operation of the embodiment of FIG. 1.
FIG. 2A is a waveform chart illustrating the appearance of an idealized waveform that might be displayed or printed by the system of FIG. 1.

With reference to the drawing, and initially to FIG. 1 thereof, the system of this invention employs a pneumotachographic mask 11, which is a device that detects the volume velocity of the airflow in a human subject's speech. Here the mask 11 is a circumferentially vented pneumotachograph mask of the type often referred to as the Rothenberg mask, and as described in Rothenberg, M., *A New Inverse-Filtering Technique For Deriving The Glottal Airflow Waveform During Voicing*, Journal of the Acoustical Society of America, Vol. 53, 1973, pages 1632-1645. The mask 11 covers the subject's nose and mouth, and can accommodate both oral and nasal airflow. The shape of the mask is not critical, but generally conforms to the shape of the face, with a compressible seal fitting against the patient's face. A number of peripheral openings on mask surfaces closet to the mouth are covered with fine mesh either of wire or other material stiff enough not to vibrate at the voice frequencies, so that the airflow moves out through these holes. The handle shown in FIG. 1 or some other contrivance allows the mask to be kept in an airtight seal with the face during the speech act. Facial hair interfering with such a seal may have to be coated with some form of grease such as petroleum jelly for an accurate recording. In an alternative arrangement that permits accurate measurements when natural speech is not required, a mask may be fit to the lips of the open mouth, and the nares closed to keep all airflow through the mouth. The mask includes a transducing device for measuring the pressure differential between the inside of the mask and immediately outside of the mask, preferably a Glottal Enterprises model MTW differential pressure transducer, which is a Microswitch type 164 transducer modified to extend the frequency response. A uniform frequency response from zero Hz (DC) to at least about three times $F_0$ is required.

The transducer output is provided through an amplifier and linear-phase low-pass filter 13 with a roll off above the range of expected values for $F_1$ to a filter 15 whose transfer function extends from below the lowest expected fundamental glottal wave frequency $F_{0L}$ (i.e., about 50 Hz) to just above the highest expected glottal frequency $F_{0H}$ (i.e., about 400 Hz). This filter 15 produces an AC wave which will almost always have only one positive-going zero crossing and only one negative-going zero crossing for each glottal period. The output of the filter 15 is supplied to a zero crossing detector 16 which determines the extent of each glottal period $T_0$ as the time interval between successive negative-going zero crossings. The output of the amplifier and filter 13 is also fed to a peak value circuit 14 which provides a measurement of the maximum or peak value P within each estimated glottal period from detector 16. The output of the amplifier and filter 13 is further fed through an approximate inverse-filter 17, which is a notch filter consisting of a single antiresonant circuit tuned to the approximate expected frequency and damping of the first formant $F_1$. The output of this filter 17 is supplied to a low-pass filter 18 which has a $-3$ dB roll off frequency $F_c$ at about half the frequency of the first formant $F_1$. An eight-pole Bessel or similar filter would be appropriate for this filter. The signal appearing at the output of the filter 18 will be a smoothed representation of the glottal waveform, and will have a negative extreme either at zero or substantially offset above zero, similar to L in FIG. 2. This output signal and the glottal period estimate from the circuit 16 are fed to a calculating circuit 19 which determines the minimum value of the output signal within each glottal period, which value represents an estimate of the airflow at the point of maximum closure of the vocal folds, a value sometimes referred to as glottal airflow leakage. A difference circuit 20 receives the peak value P from the circuit 14 and also receives the minimum value from the circuit 19, and produces an amplitude value A which corresponds to the difference between the peak and minimum values. The output signal from the low pass filter 18 is also fed to a low-pass filter whose cutoff frequency is substantially below the fundamental glottal frequency $F_0$, i.e., with a time constant greater than the glottal period $T_0$. This produces generally a slowly-varying voltage corresponding to the mean or average airflow value, as averaged over the time constant of the filter; alternatively, the mean value M can be computed over each one period by use of an integrator circuit which is set to zero at the onset of each period $T_0$. The value M from the filter 21 at a time corresponding to the end of the glottal period being measured and the minimum value L from the circuit 19 are supplied to a difference circuit 22 which produces an output signal that corresponds to the wave center value $\overline{M}$ for that glottal period, which is the difference between the mean airflow M and the minimum value. Finally, the amplitude value A and the glottal wave center value $\overline{M}$ are fed to an open quotient detecting circuit 23, which provides the value of the glottal duty cycle or open quotient $Q_0$. This open quotient $Q_0$ is calculated from $\overline{M}$ and A so as to approximate the duration of the open portion of the glottal wave B (representing the period when the vocal folds are not in contact) to the entire glottal period $T_0$.

Appropriate relationships of these values P, L, M, $\overline{M}$, A, $T_0$, B, and C are all shown on the waveform chart of FIG. 2.

In the circuit 23, the open quotient $Q_0$ can be determined as a function of the wave center value $\overline{M}$ and the wave amplitude A, according to the relationship:

$$\frac{\sin(\pi Q_0) - \pi Q_0 \cos(\pi Q_0)}{1 - \cos(\pi Q_0)} = \frac{\pi \overline{M}}{A}$$

This relationship arises from the truncated sinusoidal wave approximation as illustrated graphically in FIG. 2A.

Rather than having an intricate circuit to solve for $Q_0$ as a function of $\overline{M}$ and A directly, it is adequate to provide the values of $Q_0$ from a programmed look-up table as a function of the ratio $\overline{M}/A$.

To develop a suitable display of the measured parameters, the variables $T_0$, A, $Q_0$ and L can be input to a microcomputer or other equivalent digital processor 24 with appropriate A-D digitizing capabilities. Alternatively, the values of $T_0$, P, L and M can be input and computations performed to achieve the same functions as elements 20, 22, and 23. In either case, the microcomputer or processor can display on a video display or screen 25, or provide as hard-copy output via a printer 26, the values of the above parameters for each glottal period, either as numerical values or in graphical form as an idealized glottal waveform that has measured parameter values, such as the idealized waveform in FIG. 2A.

To render the parameter values easier for the clinician to interpret, the parameter values can also be displayed or printed as an idealized replica of the glottal waveform that has the measured parameter values. This can be a truncated sinusoid representation useable for the computation of $Q_0$. The waveform displayed or printed could be shown in FIG. 2A, in which a solid line shows the display of one period.

Figure 3:
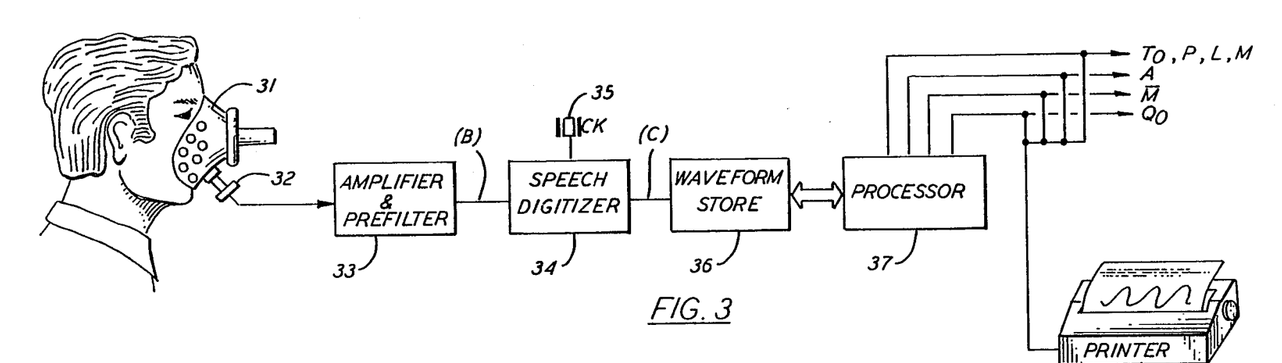
FIG. 3 is a schematic block diagram of a second embodiment of this invention.

An alternative arrangement for implementing the system of this invention is shown in the embodiment of FIG. 3. Here, a circumferentially-vented pneumotachograph mask 31 has a differential pressure transducer 32 connected to a suitable amplifier 33 which amplifies signals in the voice frequency range down to direct current and a linear-phase low-pass prefilter which removes energy substantially above $F_1$. The output of this amplifier and prefilter 33 is supplied to a digitizer or A-D circuit 34, which can include a data acquisition board within a personal computer or a similar digital processing device. The digitizer 34, which has an associated clock pulse generator 35, digitizes the input as a series of sample values, and these are stored in a waveform storage device 36, which can be a random access memory of suitable capacity. The digitized values as stored in the storage device 36 are manipulated in a suitably programmed processor 37, which automatically produces the values $T_0$, P, L, M, A, $\overline{M}$, and $Q_0$.

Figure 4A:
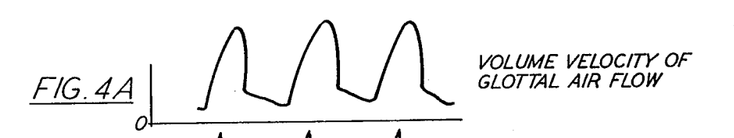
FIGS. 4A-4D are waveform charts for explaining the operation of the embodiment of FIG. 3.
Figure 4B:
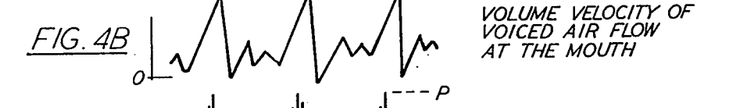
Figure 4C:
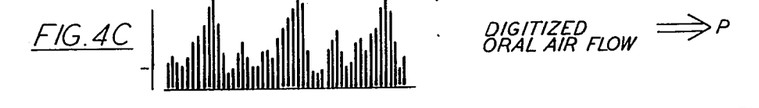
Figure 4D:
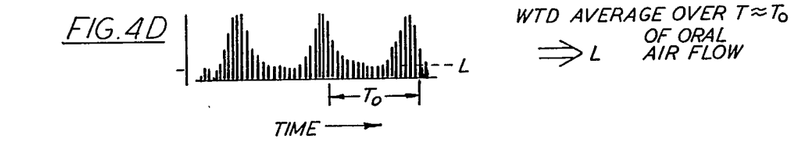

The airflow through the subject's glottis or larynx, which airflow has the general form as shown in FIG. 4A, is modified by the vocal tract resonances to produce a rather complex voice airflow which after some smoothing or low-pass filtering appears as the signal generally shown in FIG. 4B. The digitizer 34 produces corresponding digital values which appear at the output thereof as quantitized numerical estimates of the sample values (vertical bars) shown in FIG. 4C. These are stored in respectively memory locations in the waveform storage device 36. The processor 37 can perform various filtering techniques using appropriate algorithms, such as taking a weighted moving average over a selected time period which may correspond to the glottal period $T_0$, to produce a smoothed approximation of the glottal waveform, as generally shown in FIG. 4D. The digitized waveform values in 4C and 4D can be measured directly to obtain the values P, L, and $T_0$. In each of FIGS. 4A to 4D, the time variable is along the abscissa, and amplitude is along the ordinate, representing volume velocity of glottal air flow and raised air flow in FIGS. 4A and 4B. FIGS. 4C and 4D show bar-graph representations of digital values of voiced air flow and a weighted average over one period $T_0$, respectively. An average of the stored digitized signal values over any given glottal period $T_0$ will produce a mean or average flow value M. The amplitude A, the center value $\overline{M}$, and the open quotient $Q_0$ can be derived from the above, as with the first embodiment. A printer 28 can be coupled to the processor 37.

While the invention has been described in detail with respect to certain preferred embodiments, it should be understood that the invention is not limited to those precise embodiments, and that many modifications and variations would present themselves to those skilled in the art without departure from the scope and spirit of this invention, as defined in the appended claims.

What is claimed is:

1. A method for extracting voice parameters from oral or combined oral and nasal airflow produced during voiced speech, comprising the steps of:
   having a patient pronounce a voiced vowel into a pneumotachograph device that produces a first output signal representing the speech waveform of the voiced vowel, the first output signal including a component that represents the mean airflow;
   performing a low pass prefiltering operation on said first output signal to reduce energy thereof from vocal tract formants higher than the first or lowest formant;
   performing a low pass filtering operation on the prefiltered pneumotachograph first output signal to produce as a second output signal a smoothed version of a volume velocity waveform in which formants of the voiced vowel are suppressed, and which has a minimum value that approximates that of a corresponding glottal waveform produced by the air flow through the patient's glottis;
   deriving from the prefiltered signal and second output signal a maximum value P and a minimum value L, respectively, of said volume velocity waveform, and further deriving from said prefiltered signal and said second output signal a glottal wave period $T_0$ and an average value M, respectively;
   finding an amplitude A of the glottal waveform from the relationship $A = P - L$;
   finding a wave center value $\overline{M} = M - L$;
   finding an open quotient $Q_0$, which represents the ratio $Q_0 = B/T_0$ of the portion B of the glottal wave period in which the patient's glottis is open, to the entire glottal wave period $T_0$, wherein the open quotient $Q_0$ is a function of the amplitude A and the wave center value $\overline{M}$; and
   presenting a record of the values $T_0$, A, L, and $Q_0$ of the patient.

2. The method of claim 1 wherein said open quotient $Q_0$ is determined substantially according to the relationship:

$$\frac{\sin(\pi Q_0) - \pi Q_0 \cos(\pi Q_0)}{1 - \cos(\pi Q_0)} = \frac{\pi \overline{M}}{A}$$

3. The method of claim 2 wherein the value of $Q_0$ is derived from a look-up table based on the corresponding values of $\overline{M}$ and A.

4. The method of claim 1 wherein said low-pass filtering operation includes passing the pneumotachograph output signal through a linear-phase filter to eliminate first and higher formants without appreciably time shifting any frequency component relative to a fundamental component of the glottal waveform.

5. The method of claim 4, said step of performing a low pass filtering operation comprising passing the pneumotachograph first output signal through a predetermined inverse-filtering means which reduces substantially the energy at a first formant $F_1$ in the voiced vowel speech waveform, and then passing the inverse-filtered signal therefrom through a low pass filter.

6. The method of claim 5 wherein said low pass filter has a time constant greater than the glottal wave period $T_0$ to produce said average valve M which corresponds to the mean air flow of the voiced vowel.

7. The method of claim 1 in which said low-pass filtering operation includes digitizing the pneumotachograph output signal to produce a series of sampled digital values, and selectively combining the sampled digital values to produce suitable derived waveforms from which the values of P, L, and M can be taken.

8. The method of claim 7 in which a smoothed glottal waveform is produced as a weighted moving average of sampled values taken over a predetermined time period.

9. The method of claim 1 wherein said step of presenting a record of the values P, L, $Q_0$ includes synthesizing a representation of the patient's glottal waveform from the parameter values $T_0$, P, L, and $Q_0$.

10. Apparatus for extracting voice parameters from oral or combined oral and nasal air flow produced during voiced speech, comprising
   a pneumotachographic instrument into which a patient pronounces a voiced vowel and having an output that produces an output signal representing a volume velocity airflow waveform for the voiced vowel including a signal component that represents the mean air flow;
   low pass filter means having an input coupled to said penumotachographic instrument output which filters said output signal to produce a prefiltered waveform in which frequencies higher than the first formant frequency of the pronounced vowel are suppressed;
   signal processing means having inputs to receive the prefiltered waveform and which derives therefrom a peak value P, minimum value L, glottal wave period $T_0$, and mean air flow value M for a glottal waveform;
   calculating means input with values P, L, $T_0$, and M for finding an amplitude A of the glottal waveform from the relationship $A = P - L$; and for finding a wave center value $\overline{M}$ from the relation $\overline{M} = M - L$;
   calculating means for finding an open quotient $Q_0$ which represents the ratio $Q_0 = B/T_0$, where B is the open portion of the glottal wave period in which the patient's glottis is open and $T_0$ is the entire glottal wave period, wherein the open quotient $Q_0$ is a function of the amplitude A and wave center value $\overline{M}$; and means for presenting a record of the values $T_0$, P, L, and $Q_0$ of the patient.

11. The apparatus of claim 10 wherein said open quotient $Q_0$ is derived substantially according to the relationship:

$$\frac{\text{Sin}(\pi Q_0) - \pi Q_0 \text{Cos}(\pi Q_0)}{1 - \text{Cos}(\pi Q_0)} = \frac{\pi M}{A}$$

12. The apparatus of claim 10 wherein said pneumotachographic instrument includes a Rothenberg circumferentially-vented pneumotachographic mask.

13. The apparatus of claim 10 wherein said low-pass filter means includes a low-pass filter having an input coupled to receive the output signal of the pneumotachographic instrument an an output, a band-pass filter coupled to the output of said low-pass filter having a pass band that extends from the lowest frequency $F_{0L}$ to the highest frequency $F_{0H}$ expected for the fundamental frequency of the glottal wave of said pronounced vowel, and producing an output signal, and a zero-crossing detector which measures the period $T_0$ of the glottal waveform from the output signal of said band-pass filter.

14. The apparatus of claim 13 wherein the input of a peak detector circuit is coupled to the output of the said prefilter circuit and said zero crosssing detector to derive the peak glottal airflow P from the peak value of the prefilter output within the glottal period obtained from the zero crossing detector.

15. The apparatus of claim 14 wherein said low-pass filter means further includes an approximate inverse-filter circuit coupled to the output of said low-pass filter means and for reducing the energy at and near the first formant frequency $F_1$ of said vowel, followed by a second low-pass filter having a roll-off frequency below the lowest expected said first formant frequency but well above the highest expected $F_{0H}$, and said calculating means includes means coupled to the output of said second low-pass filter and to said zero-crossing detector to derive the minimum value L of the glottal airflow.

16. The apparatus of claim 15 wherein said low pass filter means further includes a third low-pass filter coupled to the output of the second low-pass filter and having a roll-off frequency below the lowest expected frequency $F_{0L}$ of the glottal waveform for producing the value M of mean glottal airflow.

17. The apparatus of claim 16 wherein said calculating means includes subtraction means for combining the peak value P and minimum value L of said glottal waveform to produce the amplitude value A, and for combining the mean glottal airflow value M and the glottal waveform minimum value L to produce the wave center value $\overline{M}$.

18. The apparatus of claim 10, wherein said low-pass filter means includes means for digitizing the output of said pneumotachographic instrument as a sequence of numerical samples values, and means for selectively combining the numerical samples to produce a derivative sequence of values representing the glottal waveform, from which can be measured the values of $T_0$, P, L, and M.

19. The apparatus of claim 18 comprising a programmed microprocessor device for processing said sequence of numerical sample values and calculating the values $T_0$, P, L, M, A, $\overline{M}$, and $Q_0$.

* * * * *

UNITED STATES PATENT AND TRADEMARK OFFICE
CERTIFICATE OF CORRECTION

PATENT NO. : 4,862,503

DATED : August 29, 1989

INVENTOR(S) : Martin Rothenberg

It is certified that error appears in the above—identified patent and that said Letters Patent is hereby corrected as shown below:

At column 1, line 4, please insert:

--This invention was made with government support under Grant No. R01 NS-08919 awarded by the National Institutes of Health. The Government has certain rights in the invention.--

Signed and Sealed this

Twenty-second Day of December, 1992

Attest:

DOUGLAS B. COMER

Attesting Officer      Acting Commissioner of Patents and Trademarks